United States Patent [19]

Fairhurst

[11] Patent Number: 5,252,066
[45] Date of Patent: Oct. 12, 1993

[54] ORTHODONTIC BRACKET FORMED FROM PORCELAIN FUSED TO METALLIC MATERIAL

[75] Inventor: Carl W. Fairhurst, North Augusta, S.C.

[73] Assignee: Johnson & Johnson Consumer Products, Inc., Skillman, N.J.

[21] Appl. No.: 936,977

[22] Filed: Aug. 28, 1992

[51] Int. Cl.$^5$ .............................................. A61C 3/00
[52] U.S. Cl. .............................................. 433/8; 433/9
[58] Field of Search ........................................ 433/8, 9

[56] References Cited

U.S. PATENT DOCUMENTS

| 3,052,983 | 9/1962 | Weinstein | 32/12 |
| 4,050,156 | 9/1977 | Chasanoff et al. | 433/8 X |
| 4,107,844 | 8/1978 | Kurz | 433/9 |
| 4,459,263 | 7/1984 | Prasad | 430/437 |
| 4,483,821 | 11/1984 | Prasad | 420/437 |
| 4,735,569 | 4/1988 | Munk | 433/9 |
| 4,988,293 | 1/1991 | Collins et al. | 433/9 X |
| 5,011,410 | 4/1991 | Culler et al. | 433/180 X |
| 5,032,081 | 7/1991 | Farzin-Nia et al. | 433/8 |
| 5,074,783 | 12/1991 | Reher | 433/8 |
| 5,078,596 | 1/1992 | Carberry et al. | 433/9 X |
| 5,096,417 | 3/1992 | Greenberg et al. | 433/9 X |

Primary Examiner—Gene Mancene
Assistant Examiner—Nicholas D. Lucchesi
Attorney, Agent, or Firm—Paul A. Coletti

[57] ABSTRACT

A metal bracket is provided with a covering formed for dental porcelain. The porcelain is placed on the sides and buccal surfaces of the bracket and provides for an aesthetic appearance to the bracket. However, the high strength is provided by the metal. The exposed metallic surfaces of the archwire slot and base enable the bracket to function in the manner of a metal bracket. This porcelain fused to metal bracket enables the user to derive the best possible functions of both types of materials.

15 Claims, 1 Drawing Sheet

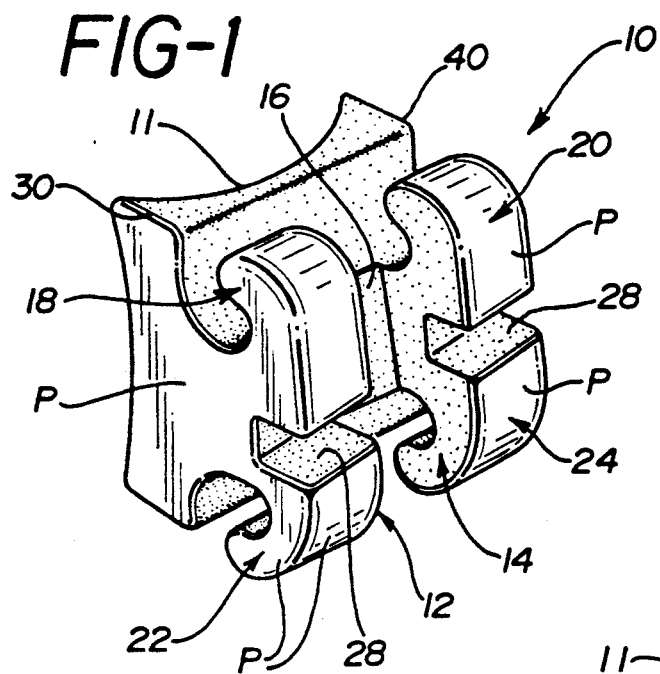
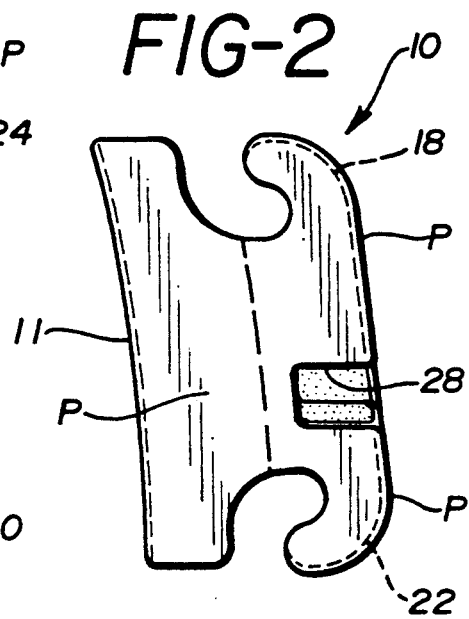
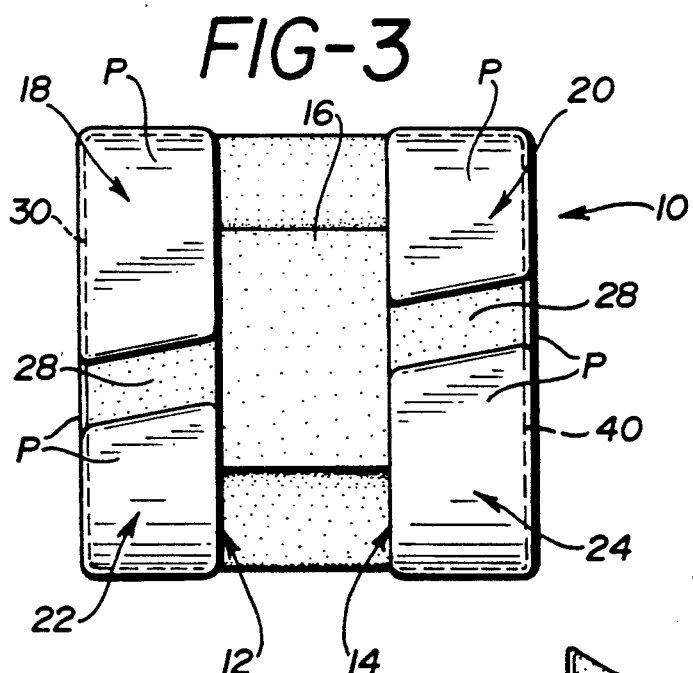
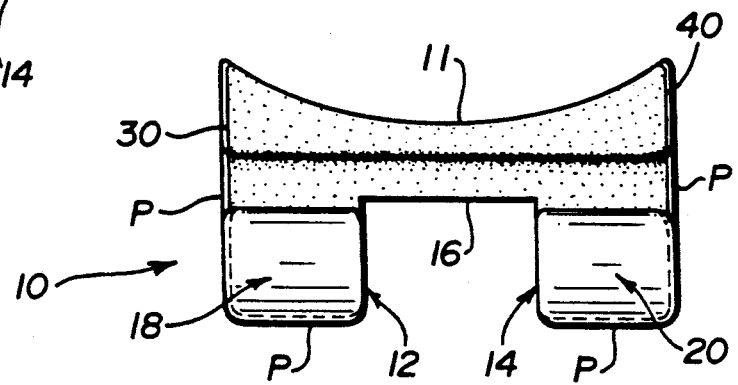

ORTHODONTIC BRACKET FORMED FROM PORCELAIN FUSED TO METALLIC MATERIAL

FIELD OF THE INVENTION

Generally, this invention relates to a new type of orthodontic bracket. Specifically, this invention describes a new type of metal dental bracket with an aesthetic appearance. More specifically, this invention relates to an aesthetic dental bracket made out of metal which has porcelain fused to its outward faces (PFM) so that the porcelain provides an aesthetic appearance.

BACKGROUND OF THE INVENTION

Dental porcelains are specific formulations of a class of ceramics called porcelains that were produced in China and other countries by 1500 A.D.

In Philadelphia in 1844, Samuel Stockton White began the manufacture of porcelain teeth for dentures. These high quality teeth were refined during the next 125 years and are still made in large quantities. During that time other uses for dental porcelain were developed requiring modification of the basic composition containing the minerals feldspar, quartz and kaolin. Potash and soda are added for special properties. These denture tooth porcelains were high fusing, 2375°–2550° F. (1300°–1400° C.). Single tooth crowns were also made from porcelain with little or no kaolin resulting in a lower fusing temperature and greater translucency.

Dental porcelains used for coating metals are feldspar glasses resulting from compositions of about 55% silica, 12% aluminum oxide, 14% potash and soda and various oxides for color and translucency control. As result of the composition, these porcelains all contain crystalline lucite particles. Lucite is the high thermal expansion component, 21 PPM/°C. (parts per million per degree Celsius). The low thermal expansion, 9 PPM/°C., is the glassy component, which when combined with the lucite provides the proper thermal expansion for the porcelains to fuse to metal alloys. These porcelains have been fused to metals that have thermal coefficients of expansion that are similar to the porcelains of the proper composition. Examples of such metals are gold-platinum-palladium, palladium-silver, cobalt-chromium, nickel-chromium and others. Failure to properly match the metal and porcelain with regard to the thermal expansion will result in cracking and spalling of the porcelain coating.

Porcelains used for PFM applications fuse between 1650°–1850° F. (900°–1010° C.) which are considered low fusing porcelains. These porcelains are capable of being colored and tinted to match the appearance of natural teeth. They are relatively insoluble in mouth fluids and remain aesthetic for many years.

Although enamels, glasses and ceramic coatings had been used in many prior applications, the concept of "matched thermal coefficients of expansion" for specific porcelains and metals for dental crowns must be credited to the Weinsteins.

Weinstein et al., U.S. Pat. Nos. 3,052,982 and 3,052,983, demonstrate that by special formulations of $Si)_2Al_2O_3$ and potassium and/or sodium oxides a porcelain can be obtained that is thermally compatible with certain dental gold alloys to make prosthetic teeth. This means that the thermal coefficients of contraction of the metal and porcelain must be sufficiently similar to prevent spalling and fracture of the coating during cooling. A second requirement is that the molten glassy porcelain must wet the metal and in particular its oxide covered surface. The wetting is necessary but not sufficient. When the porcelain and metal cool to room temperature the porcelain must strongly adhere to the metal. Much research over the last 30 years has dealt with all of these requirements that must be met by the porcelain and alloy to be successful. Gold alloys were the metal of choice at the time. Since then many nonprecious metal alloys have been used to replace gold alloy.

Porcelain fused to metal (PFM) dental applications have the desirable properties of both materials; metal provides strength and toughness and porcelain provides beauty and aesthetics. The PFM technology is among the major developments in modern dentistry.

Nickel-chromium alloy for prosthodontic applications has become, over the last ten years, the major alloy in that field. During this time numerous other alloys have also been used for PFM applications. These alloys include cobalt-chromium, iron-chromium, and combinations of these and nickel-chromium alloys with molybdenum and beryllium. Many alloys containing gold, platinum palladium and silver have been used since 1962.

There has been no known attempt to use these alloys for dental brackets. The stainless steel alloy currently in use in orthodontics for manufacturing brackets has been traditionally accepted. However, stainless steel is not an alloy that meets all of the requirements of a PFM application.

SUMMARY OF THE INVENTION

It is therefore an object of the present invention to describe a new use for porcelain fused to metal technology by the use of dental brackets with porcelain fused to metals for an aesthetic appearance.

It is further an object of the present invention to provide a dental bracket wherein the porcelain fused to metal is placed on the bracket only in the aesthetics areas, such as tie wings.

It is further an object of the invention to provide a dental bracket wherein the porcelain fused to metal is devoid in the areas where there is high repetitive usage during dental tooth management, such as archwire slots and base pads, as well as the rear of the tie wings.

These and other objects of the invention are included in a dental bracket. In general, the dental bracket will have a pair of tie wings separated by a saddle. Also, there is an archwire slot which divides the tie wings into mesial and gingival halves. The dental bracket itself has a face which faces the buccal surface of the mouth. This face is generally covered by porcelain fused to metal. The dental bracket has no porcelain adhered to the surfaces of high usage such as the rear of the tie wings, the base or the archwire slot. The typical type bracket is a nickel-chromium alloy dental bracket or perhaps other appropriate metals. It has been applied to it the porcelain in slurry form which is then fired and glazed to produce an aesthetic surface. What is finally produced is an aesthetic bracket which has all the strength properties of metal, and yet the aesthetic properties of porcelain.

These and other objects of the invention will better be understood by reference to the attached figures taken in conjunction with the detailed description of the invention.

DETAILED DESCRIPTION OF THE FIGURES

FIG. 1 is a perspective view of the dental bracket of this invention;

FIG. 2 is a side view of the dental bracket of this invention;

FIG. 3 is a cross-sectional view of the dental bracket as taken across lines 3—3 of FIG. 1; and FIG. 4 is a perspective view of the dental bracket of this invention.

DETAILED DESCRIPTION OF THE INVENTION

There is described a dental bracket 10 having pad 11 supporting a pair of tie wings 12, 14 separated by a saddle 16. This saddle 16 generally divides the dental bracket in half. Each of the tie wings have tips on the gingival side 18, 20. Further, each of the tie wings have tips on the mesial side 22, 24. Archwire slot 28 separates these tips. This bracket 10 is indicative of the state-of-the-art dental brackets, including the brackets such at the Mini-Twin TM sold by "A" Company, 11436 Sorrento Valley Road, San Diego, Calif. 92121.

As further seen from FIGS. 2 and 3, bracket 10 also has side walls 30, 40. Each of these side walls is formed on the side of one of the tie wings 12, 14. The side walls 30, 40 are also formed out of the same metallic material as the entire dental bracket 10, so that the dental bracket is generally a one-piece material.

It is typical for the dental brackets to be formed from nickel-chromium alloys or even more ideally from stainless steel. Stainless steel provides for the ultimate strength of material necessary for dental bracket formulations. However, nickel-chromium alloy has proven to be quite an ideal substitute, especially in the use of porcelain fused to metal technology.

The glass enameled metal or porcelain that is used in this invention is the typical dental porcelain found in many uses in the dental technology. As better seen in FIGS. 1, 2, 3 and 4, there is fused to the surfaces of the dental bracket this porcelain material P. Ideally, the porcelain material is placed on each of the front facing or buccal surfaces of the tie wings 12, 14, as well as the sides 30, 40 of the dental bracket 10. It has been found that porcelain of a coating from 0.001 inches to about 0.010 inches is ideal for the aesthetic purposes of the porcelain. A very light coating, generally 0.003 inches thick is formed of this porcelain material.

It will be noticed that the archwire slot 26, the area under the tie wings 12, 14 and the pad surface forming the rear of the dental bracket are not coated. This ensures proper function of the bracket 10 as well as the thicknesses desirable for dental corrective purposes. This is also believed to be unique to any current dental bracket in that while aesthetic, the dental bracket has the necessary characteristics of controlled tolerances for proper treatment.

A dental bracket is ideally formed by casting an appropriate alloy for porcelain fused to metal technology. Precise control of compensating for the metal shrinkages during casting must be maintained to preserve the accuracy of the dental bracket. Two methods of such control are the liquid/powder ratio of the mold refractory material and the temperature of the mold, 1600°–1800° F. at the time of casting. These two variables will depend upon the selection of the mold material and the alloy to be used for the bracket.

While the ideal design of the porcelain fused to metal bracket is the porcelain fused to nickel-chromium alloy, several of which are provided by a number of manufacturers including Jeneric/Pentron Inc., it is also intended that porcelain fused to such materials as titanium alloys, gold-platinum-palladium alloys, palladium-silver alloys, chromium-cobalt-iron alloys, cobalt-chromium alloys with or without the following constituents: nickel, aluminum, yttrium, molybdenum, beryllium, tungsten, niobium, manganese, gallium or zirconium be disclosed by this Specification. This will be better understood and determined from the following example of typical porcelain fused to metal bracket technology.

EXAMPLE I

A dental bracket of the type such as the Mini-Twin TM bracket sold by "A" Company, San Diego, Calif. is prepared for application of porcelain by cleaning the surfaces with abrasive blasting with aluminum oxide. The bracket is then heated in vacuum from 1200°–1800° F. at 100° F. per minute to de-gas the surface. The surface should not be touched prior to porcelain application. Then the surfaces such as those within the archwire slot, behind the tie wings and the base that are not to receive porcelain are carefully protected with, for example, an adhesive covering or by other means of shielding the surfaces from the porcelain.

Thereafter, the porcelain provided by one of a number of manufacturers, including Dentsply International, York, Pa. in a powdered form is mixed with a liquid to form a slurry suitable for application. The liquid can be water or mixtures of one of the common alcohols and water. The slurry can be applied painting the surface with a small brush or spraying. Either method can produce suitable coatings. It is found that a coating of about 0.003" to 0.006" is required to obtain an aesthetic appearance yet not make the bracket too bulky. It has been found that translucency and the shade or color of the specific porcelain can affect the esthetics of the PFM bracket. Thereafter the adhesive or shielding is removed from the bracket surfaces as deemed necessary and the bracket is placed in a dental porcelain furnace, commonly found in dental laboratories, and heated in a manner prescribed by the porcelain manufacturer. The bracket is then sterilized for usage.

What has been found is that this bracket has aesthetic properties such as many of the ceramic type brackets because of the use of porcelain. However, because of its high strength (with use of metal) and the availability of bare surfaces: (1) in the archwire slot; and (2) behind the tie wings for placing ligatures and archwire; as well as (3) in the rear surface for placing adhesive to adhere the bracket to the teeth, this bracket also has all the metallic characteristics necessary for high strength dental brackets.

Therefore, the present invention is useful for aesthetic and high strength purposes. It is to be realized that any one of a number of equivalents such as other alloys or other types of aesthetic materials are useful for the current bracket in order to continue with the desired aesthetic purposes of this bracket, such as ceramics or polymeric/glass composites. What is therefore to be realized is that the invention to be described by the attached claims and any equivalents.

What is claimed is:

1. A dental bracket formed from metal, and having a tooth facing surface, a pair of sides attached to said tooth facing surface, and a buccal surface attached to said pair of sides and forming an archwire slot between said sides, wherein said buccal surface has fused to it a coating of dental porcelain and said slot having an exposed metallic surface.

2. The dental bracket of claim 1 wherein said coating is also applied to said pair of sides.

3. A metal dental bracket comprising:
a base containing a tooth facing surface;
a pair of tie wings supported by said base, said tie wings having a mesial tip and a gingival tip and separated by an archwire slot, and said tie wings each having a pair of sides, said tie wings separated by a saddle; and
said tie wings containing a rear portion which with said base forms a ligature placement area; and
said archwire slot placed transversely across said tie wings;
wherein said tie wings are coated with a layer of aesthetic dental coating; and
wherein the coating is formed from a porcelain specified for porcelain fused to metal technology.

4. The dental bracket of claim 3 wherein said rear portion is exposed metal.

5. The dental bracket of claim 3 wherein said archwire slot is exposed metal.

6. The dental bracket of claim 3 wherein said metal contains at least 0.5 weight percent of nickel, chromium, molybdenum and beryllium.

7. The dental bracket of claim 3 wherein said metal contains at least 0.5 weight percent of nickel, chromium and molybdenum.

8. The dental bracket of claim 3 wherein said metal containing at least 0.5 weight percent of cobalt and chromium and further containing constituents selected from the group consisting of: iron, nickel, aluminum, yttrium, molybdenum, beryllium, tungsten, niobium, manganese, gallium and zirconium.

9. The bracket of claim 3 wherein said metal is a titanium alloy.

10. The bracket of claim 3 wherein said metal contains gold, platinum, palladium, tin and indium.

11. The bracket of claim 3 wherein said metal is palladium-silver alloy.

12. The bracket of claim 3 wherein said metal is cobalt-chromium-iron.

13. A metal dental bracket comprising:
a base containing a tooth facing surface;
a pair of tie wings supported by said base, said tie wings having a mesial tip and a gingival tip and separated by an archwire slot, and said tie wings each having a pair of sides, said tie wings separated by a saddle; and
said tie wings containing a rear portion which with said base forms a ligature placement area; and
said archwire slot placed transversely across said tie wings;
wherein said tie wings are coated with a layer of aesthetic dental coating; and
wherein the coating is formed from a ceramic designed for fusing to metal.

14. A metal dental bracket comprising:
a base containing a tooth facing surface;
a pair of tie wings supported by said base, said tie wings having a mesial tip and a gingival tip and separated by an archwire slot, and said tie wings each having a pair of sides, said tie wings separated by a saddle; and
said tie wings containing a rear portion which with said base forms a ligature placement area; and
said archwire slot placed transversely across said tie wings;
wherein said tie wings are coated with a layer of aesthetic dental coating; and
wherein the coating is a polymer-glass composite.

15. A method of fusing porcelain to a metal dental bracket, said dental bracket having;
a base containing a tooth facing surface;
a pair of tie wings supported by said base, said tie wings having a mesial tip and a gingival tip and separated by an archwire slot, and said tie wings each having a pair of sides, said tie wings separated by a saddle; and
said tie wings containing a rear portion which with said base forms a ligature placement area; and
said archwire slot placed transversely across said tie wings;
said method comprising:
(a) covering said archwire slot, said rear portions of the tie wings and said base with a means of shielding the area from porcelain;
(b) applying a water-based slurry of porcelain powder on said bracket;
(c) removing said means of shielding;
(d) heating said bracket with said porcelain applied thereon;
(e) glazing said porcelain;
(f) cooling said bracket.

* * * * *